(12) United States Patent
Kim et al.

(10) Patent No.: US 7,435,819 B2
(45) Date of Patent: Oct. 14, 2008

(54) 4,5,6,7-TETRAHYDRO-[1,2]DITHIOLO[4,3-C] PYRIDINE-3-THIONE COMPOUNDS

(75) Inventors: Sang-Geon Kim, Seoul (KR); Seung-Jin Lee, Seoul (KR); Eun-Young Park, Seoul (KR); Mvong-Suk Ko, Seoul (KR); Jin-Wan Kim, Seoul (KR); Kwang-Do Choi, Gyeonggi-do (KR); Jee-Woong Lim, Gyeonggi-do (KR); Sang-Ho Lee, Gyeonggi-do (KR)

(73) Assignee: CJ Cheiljedang Corp., Seoul (KR)

( * ) Notice: Subject to any disclaimer, the term of this patent is extended or adjusted under 35 U.S.C. 154(b) by 0 days.

(21) Appl. No.: 11/664,528

(22) PCT Filed: Oct. 11, 2005

(86) PCT No.: PCT/KR2005/003369

§ 371 (c)(1),
(2), (4) Date: Apr. 3, 2007

(87) PCT Pub. No.: WO2006/080745

PCT Pub. Date: Aug. 3, 2006

(65) Prior Publication Data

US 2008/0058368 A1    Mar. 6, 2008

(30) Foreign Application Priority Data

Oct. 11, 2004    (KR) .................. 10-2004-0080955

(51) Int. Cl.
*C07D 471/02*    (2006.01)
*A61K 31/44*    (2006.01)

(52) U.S. Cl. ....................... 546/114; 514/301

(58) Field of Classification Search .............. 546/114, 546/116; 514/301
See application file for complete search history.

(56) References Cited

FOREIGN PATENT DOCUMENTS

| EP | 308909 | A2 | 3/1989 |
|----|--------|-----|--------|
| EP | 347532 | A2 | 12/1989 |
| WO | WO-01/64215 | A1 | 9/2001 |
| WO | WO-01/76604 | A1 | 10/2001 |
| WO | WO-03/066058 | A1 | 8/2003 |

OTHER PUBLICATIONS

Gompper et al Angew. Chem. Int. Eng. Ed. 1967, 6, 366-367.*
F. Z. Dorwald Side Reactions in Organic Synthesis: A Guide to Successful Synthesis Design 2005, Wiley-VCH Verlag GmbH and Co. KGaA, Wienheim.*
Beers, M. H. The Merck Manual of Medical Information, 2nd Ed., Merck Research Laboratories, Merck and Co. Inc. Whitehouse Station, NJ, 2003.*
Kang et al., 'Oltipraz regenerates cirrhotic liver through CCAAT/ enhancer binding protein-mediated stellate cell inactivation' In: FASEB Journal, 2002, 16(14), pp. 1988-1990.
Kang et al., 'The anti-fibrogenic effect of a pharmaceutical composition of oltipraz and DDB' In: Archives of Pharmacal Research, 2002, 25(5), pp. 655-663.
Kang et al., The Anti-Fibrogenic effect of a Pharmaceutical Composition of [5-(2-Pyrazinyl)-4-menthyl-1,2-dithiol-3-thione (Oltipraz) and Dimethl-4,4'-dimethoxy-5,6,5',6'-demethylene dioxybiphenyl-2,2'-dicarboxylate (DDB), Archives of Pharmacal Research, vol. 25, No. 5, pp. 655-663, May 14, 2002.
Kang et al., Oltipraz regenerates cirrhotic liver through CCAAT enhancer binding protein-mediated stellate cell inactivation, The FASEB Journal, vol. 16, pp. 1988-1990, Dec. 2002.

* cited by examiner

*Primary Examiner*—Rita Desai
*Assistant Examiner*—John Mabry
(74) *Attorney, Agent, or Firm*—Birch, Stewart, Kolasch & Birch, LLP

(57) ABSTRACT

The present invention relates to new compounds directly increasing kinase activity of p90 ribosomal S6 kinase 1 (RSK1), a pharmaceutical composition comprising them as active ingredient, a use thereof to prevent or treat hepatic fibrosis or cirrhosis, and a method for preventing or treating hepatic fiborsis or cirrhosis, comprising administering a therapeutically effective amount of the composition to mammal.

4 Claims, No Drawings

4,5,6,7-TETRAHYDRO-[1,2]DITHIOLO[4,3-C] PYRIDINE-3-THIONE COMPOUNDS

TECHNICAL FIELD

The present invention relates to new 4,5,6,7-tetrahydro-[1,2]dithiolo[4,3-c]pyridine-3-thione compounds. Particularly, the present invention relates to compounds of the following formula (I) directly increasing kinase activity of p90 ribosomal S6 kinase 1 (RSK1), a pharmaceutical composition comprising them as active ingredient, a use thereof to prevent or treat hepatic fibrosis or cirrhosis, and a method for preventing or treating hepatic fibrosis or cirrhosis, comprising administering a therapeutically effective amount of the pharmaceutical composition to mammal:

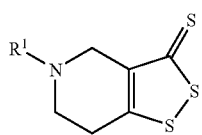

(I)

wherein the definitions of substituents are as defined in the Specification.

BACKGROUND ART

The present invention relates to new 4,5,6,7-tetrahydro-[1,2]dithiolo[4,3-c]pyridine-3-thione compounds, pharmaceutically acceptable salts thereof, or solvates or hydrates thereof. Specifically, the above 4,5,6,7-tetrahydro-[1,2]dithiolo[4,3-c]pyridine-3-thione compounds of the present invention directly activates p90 ribosomal S6 kinase 1 (RSK1) to increase its kinase activity, thereby resulting in phosphorylation of a specific residue of CCAAT-enhancer binding protein β (C/EBPβ) to form an activated form of C/EBPβ. The activated form of C/EBPβ regulates gene expression, thereby accelerating regeneration of liver cell. Also, the activated form of C/EBPβ inhibits expression of transforming growth factor β (TGFβ) which is a key factor of hepatic fibrosis, to prevent and treat hepatic fibrosrsis and cirrhosis.

Liver plays a pivotal role in metabolizing external and internal materials, and is a vital organ wherein enzyme reaction and energy metabolism continuously take place. At present, among chronic diseases in Korea, hepatitis, cirrhosis, and liver cancer are most frequent ones, along with circulatory organ diseases, and also take a big part among the causes of death due to diseases. Particularly, the population in drinking is relatively high, compared with advanced countries, and the possibility of liver damage due to heavy drinking is also high, and thus concern on the liver is high. Continuous liver tissue damage due to virus infection or drinking is a cause of chronic complex diseases which develop into cirrhosis or liver cancer. Considering physiological property and importance of liver tissue, treatment and prevention of liver diseases are very important. Thus, there has been a need to develop a technique searching and utilizing the treatment action point of a drug which can normalize liver function by reducing liver tissue damage and ultimately regenerating live cell.

The present inventors have already discovered that C/EBP's activity is an essential key transcription factor in cirrhosis treatment and live tissue regeneration through the preceding inventions [Korean Patent Application No. 2000-18134 and Korean Patent No. 0377789]. They have continuously searched a cell signal which mediates a change of expression of main genes related to hepatic fibrosis and cirrhosis. As a result, they surprisingly discovered that the compounds of formula (I) directly increase RSK1's kinase activity, and such directly increased RSK1's activity can treat hepatic fibrosis and cirrhosis. Therefore, the present inventors completed the present new compounds of formula (I) which can directly increase RSK1's kinase activity, and a pharmaceutically composition comprising them.

DISCLOSURE OF THE INVENTION

An object of the present invention is to provide new compounds directly increasing RSK1's kinase activity.

Another object of the present invention is to provide a pharmaceutical composition for the prevention or treatment of hepatic fibrosis or cirrhosis comprising the above new compounds, pharmaceutically acceptable salts thereof, or solvates or hydrates thereof, as active ingredient.

Another object of the present invention is to provide a use of the above new compounds, pharmaceutically acceptable salts thereof, or solvates or hydrates thereof for the prevention or treatment of hepatic fibrosis or cirrhosis.

Another object of the present invention is to provide a method for preventing or treating hepatic fibrosis or cirrhosis by administering a therapeutically effective amount of the above composition to mammal.

BEST MODE FOR CARRYING OUT THE INVENTION

To achieve the above objects, the present invention provides compounds of the following formula (I), pharmaceutically acceptable salts thereof, or solvates or hydrates thereof:

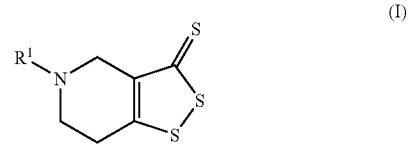

(I)

wherein
$R^1$ is selected from the group consisting of hydrogen, $C_{1-7}$alkyl, $C_{3-7}$cycloalkyl, $C_{1-7}$haloalkyl, $C_{1-7}$alkoxy, $C_{3-7}$cycloalkoxy, $C_{1-7}$alkylthio, $C_{3-7}$cycloalkylthio, $C_{1-7}$alkylsulfonyl, $C_{1-7}$alkylaminocarbonyl, hydroxyl, thiol, halogen, carboxyl, nitro, cyano, $C_{1-7}$alkylcarbonyl, $C_{1-7}$alkoxycarbonyl, $C_{1-7}$alkylcarbonyloxy, amino, $C_{1-7}$alkylamino, $C_{1-7}$alkylcarbonylamino, $C_{1-4}$alkylsulfoneamino, phenyl, heteroaryl, phenyl$C_{1-4}$alkyl and hereroaryl$C_{1-4}$alkyl, wherein phenyl is unsubstituted or substituted, wherein heteroaryl represents unsubstituted or substituted 5- or 6-membered ring containing one or more heteroatoms selected from the group consisting of nitrogen, sulfur and oxygen.

The present invention also provides a pharmaceutical composition for the prevention or treatment of hepatic fibrosis or cirrhosis comprising the compounds of formula (I), pharmaceutically acceptable salts thereof, or solvates or hydrates thereof, as active ingredient.

The present invention also provides a use of the compounds of formula (I), pharmaceutically acceptable salts thereof, or solvates or hydrates thereof for the prevention or treatment of hepatic fibrosis or cirrhosis.

The present invention also provides a method for preventing or treating fibrosis or cirrhosis, comprising administering a therapeutically effective amount of a composition comprising the compounds of formula (I), pharmaceutically acceptable salts thereof, or solvates or hydrates thereof, as active ingredient, to mammal.

Unless mentioned otherwise, the above definitions are used as follows:

halo is generic name of fluoro, chloro, bromo and iodo;

$C_{1-4}$alkyl defines straight and branched chained saturated hydrocarbon radicals having from 1 to 4 carbon atoms such as methyl, ethyl, propyl, n-butyl, 1-methylethyl, 2-methylpropyl, 1,1-dimethylethyl, etc.;

$C_{1-7}$alkyl includes $C_{1-4}$alkyl (as defined above) and higher homologues thereof having 5 to 7 carbon atoms such as 2-methylbutyl, n-pentyl, dimethylpropyl, n-hexyl, 2-methylpentyl, heptyl, etc.;

$C_{3-7}$cycloalkyl encompasses cyclic hydrocarbon having 3 to 7 carbon atoms such as cyclopropyl, cyclobutyl, cyclopentyl, cyclopentenyl, cyclohexyl, cyclohexenyl, cycloheptyl, etc.; and $C_{1-7}$alkoxy encompasses straight and branched chained alkoxy such as methoxy, ethoxy, propoxy, isopropoxy, butoxy, isobutoxy, secondary butoxy, tertiary butoxy, pentyloxy, hexyloxy, etc.

In the above compounds, preferable non-limiting substituents are not limited to halogen (e.g. chlorine, bromine, fluorine, and iodine), preferably, alkyl, alkoxy, aralkyl, or haloalkyl (e.g. fluoromethyl, difluoromethyl, trifluoromethyl, 2,2,2-trifluoroethyl, 2,2,3,3,3-pentafluoropropyl, etc.), nitro, amino, alkylamino, cyano, formyl, acyl, aminoalkyl, mono- or di-alkylaminoalkyl, azide, carboxy, alkoxycarbonyl, carbamoyl, alkylcarbamoyl, etc.

Pharmaceutically acceptable addition salts comprise pharmaceutically acceptable acid addition salts and pharmaceutically acceptable base addition salts. The pharmaceutically acceptable acid addition salts as mentioned in this specification include therapeutically active non-toxic acid addition salt forms which the compounds of formula (I) can form. The compounds of formula (I) which have basic properties can be converted into their pharmaceutically acceptable acid addition salts by treating said base form with appropriate acid. Appropriate acid includes inorganic acids, for example, hydrohalic acids such as hydrochloric or hydrobromic acid, sulfuric acid, nitric acid, phosphoric acid, etc.; or organic acids, for example, acetic acid, trifluoroacetic acid, propanoic acid, hydroxyacetic acid, lactic acid, pyruvic acid, oxalic acid, malonic acid, succinic acid (i.e. butanedioic acid), maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-amino-salicyclic acid, pamoic acid, etc.

The compounds of formula (I) which have acidic properties can be converted into their pharmaceutically acceptable base addition salts by treating said acidic form with appropriate organic or inorganic base. Appropriate base salt form includes ammonium salts; alkali or alkali earth metal salts, such as lithium, sodium, potassium, magnesium, calcium salts, etc.; salts with organic base such as benzathine, N-methyl-D-glucamine, hydrabamine salts; and salts with amino acid, such as arginine, lysine, etc.

The present invention also includes hydrates and solvates which the compounds of formula (I) can form. The hydrates and solvates can be prepared by conventional methods.

In the present invention, suitable compounds among the compounds of formula (I) are 5-benzyl-4,5,6,7-tetrahydro-1, 2-dithiolo[4,3-c]pyridine-3-thion or 3-thioxo-6,7-dihydro-3H,4H-1,2-dithiolo[4,3-c]pyridine-5-carboxylic acid ethyl ester.

The present invention was based on the novel finding that the compounds of formula (I) which directly activates RSK1 are effective for accelerating regeneration of live tissue and inhibiting expression of transforming growth factor. In fact, according to the Experimental Example below, direct increase of RSK1's activity by the compounds of formula (I) selectively phosphorylated $^{105}$Serine residue of C/EBPβ which is a key factor for cell regeneration, and C/EBPβ activated therefrom increases or inhibits activity of the target gene, thereby increasing the treatment effect on cirrhosis.

The technique according to the present invention is effective for transforming growth factor inhibition and liver cell regeneration, and so is an advanced technique for treating hepatic fibrosis and cirrhosis. In addition, the increase of RSK1's activity hardly has any side effect, and so the present technique can be utilized for the purpose of prevention as well as treatment. Furthermore, differently from a technique which deletes a specific gene, the present invention increases RSK1's activity by the compounds of formula (I), and so can decrease RSK1's activity to a desired level by stopping administration of the compounds of formula (I). Thus, when the treatment is completed, the technique of the present invention can readjust RSK1's activity.

In addition, the compounds of the present invention can be administered by formulating them in unit dosage forms suitable for oral administration and injections according to conventional methods in the pharmaceutical field. Formulations suitable for oral administration may include hard and soft capsules, tablets, powders, suspensions, syrups and the like. These formulations for oral administration may contain one or more pharmaceutically inert conventional carriers and additional additives, such as excipients like starch, lactose, carboxy methyl cellulose, kaolin, etc.; binders like water, gelatin, alcohol, glucose, arabia gum, tragacant rubber, etc.; disintegrants like starch, dextrin, sodium alginate, etc.; lubricants like talc, stearate, magnesium stearate, fluid paraffin, etc., in addition to two or more pharmacologically active ingredients. To the present invention, a solubility aid may be also added.

The effective daily amount of the present composition may vary, depending on various factors such as degree of progress of diseases in subject, time of attack, age, condition of patient, complication, etc. However, generally, it is preferable to administer the present composition to adult by 1~500 mg/kg, preferably 30~200 mg/kg, divided into several times a day.

Hereinafter, the present invention will be described in more detail with reference to the following Examples and Experimental Examples, but the scope of the present invention should not be construed to be limited thereby in any manner.

EXAMPLE 1

Preparation of 5-benzyl-4,5,6,7-tetrahydro-1,2-dithiolo[4,3-c]pyridine-3-thion (Compound 1)

0.69 g of potassium t-butoxide (6.15 mmol) was suspended in a mixed solvent of 10 ml of tetrahydrofuran and 2 ml of dimethylformamide, and 0.5 ml of 1-benzyl-4-piperidone (2.80 mmol) was added thereto and stirred at room temperature for 15 min. 0.19 ml of carbon disulfide (3.16 mmol) was added thereto and stirred at room temperature for 15 min, and then 0.89 ml of hexamethyldisylathian (4.22 mmol) was added thereto and stirred for 15 min. The reaction solution was cooled to 0° C., and 0.73 g of hexachloroethan (3.08 mmol) was added thereto and stirred at the same temperature for 30 min. 5 ml of methanol was added thereto and stirred at room temperature for 15 min to complete the reaction, and the solvent was distilled under reduced pressure and removed. The residue was diluted with 30 ml of water, extracted with 30 ml of $CH_2Cl_2$, washed with brine once, and dried with anhydrous sodium sulfate. Then, the solvent was distilled under reduced pressure, and the obtained residue was purified by column chromatography over silica gel (eluent: normal hexane/acetone=20/1), to obtain 260 mg of the desired compound in solid (33.3%)

$^1$H NMR (400 MHz, $CDCl_3$) 2.65 (t, J=3 Hz, 2H), 2.85 (t, J=3 Hz, 2H), 3.50 (s, 2H), 3.70 (s, 2H), 7.20-7.30 (m, 5H)

Mass (FAB) 280.0 ($M^{+1}$)

EXAMPLE 2

Preparation of 3-thioxo-6,7-dihydro-3H,4H-1,2-dithiolo[4,3-c]pyridine-5-carboxylic acid ethyl ester (Compound 2)

0.82 g of potassium t-butoxide (7.31 mmol) was suspended in a mixed solvent of 10 ml of tetrahydrofuran and 2 ml of dimethylformamide, and 0.5 ml of ethyl-4-oxo-1-piperidine carboxylate (3.31 mmol) was added thereto and stirred at room temperature for 15 min. 0.22 ml of carbon disulfide (3.66 mmol) was added thereto and stirred at room temperature for 15 min, and then 1.05 ml of hexamethyldisylathian (4.98 mmol) was added thereto and stirred for 15 min. The reaction solution was cooled to 0° C., and 0.86 g of hexachloroethan (3.63 mmol) was added thereto and stirred at the same temperature for 30 min. 5 ml of methanol was added thereto and stirred at room temperature for 15 min to complete the reaction, and the solvent was distilled under reduced pressure and removed. The residue was diluted with 30 ml of water, extracted with 30 ml of $CH_2Cl_2$, washed with brine once, and dried with anhydrous sodium sulfate. Then, the solvent was distilled under reduced pressure, and the obtained residue was purified by column chromatography over silica gel (eluent: ethyl acetate/normal hexane=1/10), to obtain 390 mg of the desired compound in solid (45.0%)

$^1$H NMR (400 MHz, $CDCl_3$) 1.25 (t, J=7 Hz, 3H), 2.55 (q, J=7 Hz, 2H), 2.85 (m, 1H), 3.70-3.75 (m, 3H), 4.15-4.20 (m, 2H)

Mass (EI) 261.0 ($M^+$)

EXPERIMENTAL EXAMPLE

Activation of C/EBPβ by Compound 1 and Compound 2, and Induced Expression of GSTA by C/EBPβ Activation The present experimental example is to confirm C/EBPβ activation by using Compound 1 and Compound 2 which were prepared in the above Examples, and a degree of increase of Glutathione S-transferase A (GSTA), a representative gene which is induced by C/EBPβ activation. First, among newly prepared compounds, in order to select compounds which do not kill cells, liver cell lines were added with each prepared compound (30 μM), and cultured for 24 hours. 0.7 mg/ml of MTT (yellow tetrazolium salt) was added thereto and further cultured for 4 hours. Since MTT is reduced to insoluble formazan crystal in survived cells, the produced crystal was dissolved with DMSO solvent, and the absorbance at 595 nm was measured. The cells were cultured with the newly prepared compounds except for the compounds which kill cells, i.e., Compound 1 and Compound 2 (each 30 μM), for 24 hours, and C/EBPβ activation and GSTA expression in nuclear fractions or lysates obtained from the treated cells were measured by immunochemical method.

Method for Measuring C/EBPβ Activation and Result

When C/EBPβ gene is deleted in animals, regeneration of live tissue is impossible [Greenbaum et al., J Clin Invest. 1998; 102(5):996-1007]. C/EBPβ activation inhibits transforming growth factors (TGF-β) which is a mediating factor of hepatic fibrosis [Kang et al., FASEB J. 2002; 16(14):1988-90]. Therefore, C/EBPβ activation plays an important role in liver tissue regeneration and hepatic fibrosis inhibition. C/EBPβ activation process takes place by mediating phosphorylation of specific amino acid residue, i.e., $^{105}$Serine residue of C/EBPβ [Buck et al., Mol. Cell. 1999; 4(6):1087-92]. Under this background art, it was observed whether or not direct increase of RSK1's activity by the compounds of the present invention induces phosphorylation of $^{105}$Serine residue of C/EBPβ. When the cells were treated with each of Compound 1 and Compound 2, and cultured for a specific period of time, phosphorylation of $^{105}$Serine residue of C/EBPβ was increased after 3 hours from the culture. p-C/EBPβ ($^{105}$Serine) which had been quantitatively increased by Compound 1 and Compound 2 in the cytoplasmic fractions was moved into the nuclear fractions after 6 hours. In contrast, the degree of phosphorylation of $^{188}$Threonine residue of C/EBPβ was not changed at all, from which it was confirmed that phosphorylation of C/EBPβ due to RSK1's activation by micro-molecular organic compounds only selectively takes place at specific residue of C/EBPβ molecule. In this experimental example, oltipraz was used as comparative example. As shown in Table 1 below, Compound 1 and Compound 2 showed to activate C/EBPβ (+, similar activation effects to oltipraz; ++, stronger activation effects than oltipraz). These new compounds causing C/EBPβ activation remarkably increased GSTA expression by C/EBPβ activation (O, same enzyme induction as oltipraz; OO, stronger enzyme induction than oltipraz), as anticipated.

TABLE 1

| Prepared compound | Cell death | C/EBPβ activation | GSTA induction |
|---|---|---|---|
| 1 | – | O | ++ |
| 2 | – | O | ++ |

FORMULATION EXAMPLE 1

| CJ-12108 | 100 mg |
|---|---|
| Lactose | 50 mg |
| Starch | 10 mg |
| Magnesium Stearate | proper quantity |

The above-mentioned ingredients were mixed, and compressed according to conventional tableting method to give tablet.

FORMULATION EXAMPLE 2

| | |
|---|---|
| CJ-12120 | 200 mg |
| Lactose | 50 mg |
| Starch | 10 mg |
| Magnesium Stearate | proper quantity |

The above-mentioned ingredients were mixed, and compressed according to conventional tableting method to give tablet.

FORMULATION EXAMPLE 3

| | |
|---|---|
| CJ-12108 | 50 mg |
| Lactose | 30 mg |
| Starch | 28 mg |
| Talc | 2 mg |
| Magnesium Stearate | proper quantity |

The above-mentioned ingredients were mixed, and filled in a hard gelatin capsule according to conventional preparation method for capsule to give capsule.

FORMULATION EXAMPLE 4

| | |
|---|---|
| CJ-12120 | 250 mg |
| Lactose | 30 mg |
| Starch | 20 mg |
| Magnesium Stearate | proper quantity |

The above-mentioned ingredients were intimately mixed, filled in a pack coated with polyethylene, and sealed to give powder.

INDUSTRIAL APPLICABILITY

As can be seen from the above, the compounds of formula (I) according to the present invention directly increase RSK1's activity, which in turn inhibits expression of transforming growth factor and also shows unique pharmacological effects in molecular level not only for treating cirrhosis but also accelerating regeneration of live tissue, and thus the present compounds activating RSK1 can be used as an agent for the prevention or treatment of hepatic fibrosis or cirrhosis.

What is claimed is:

1. A compound of formula (I), pharmaceutically acceptable salts thereof:

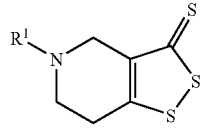

(I)

wherein
R$^1$ is C$_{1-7}$alkoxycarbonyl, or phenylC$_{1-4}$alkyl.

2. The compound according to claim 1, wherein the compound is 5-benzyl-4,5,6,7-tetrahydro-1,2-dithiolo[4,3-c]pyridine-3-thion or 3-thioxo-6,7-dihydro-3H,4E1-1,2-dithiolo[4,3-c]pyridine-5-carboxylie acid ethyl ester.

3. A pharmaceutical composition for the treatment of hepatic fibrosis or cirrhosis comprising the compound of claim 1 or pharmaceutically acceptable salts thereof as active ingredient.

4. A method for treating fibrosis or cirrhosis, comprising administering a therapeutically effective amount of the compound of claim 1 or pharmaceutically acceptable salts thereof to mammal.

* * * * *